US009522942B2

(12) United States Patent
Ladram et al.

(10) Patent No.: US 9,522,942 B2
(45) Date of Patent: Dec. 20, 2016

(54) ANALOGS OF TEMPORIN-SHA AND USES THEREOF

(75) Inventors: Ali Ladram, Ermont (FR); Denis Sereno, Poussan (FR); Feten Abbassi, Beja (TN); Bruno Oury, Vendargues (FR); Mohamed Amiche, Noisiel (FR); Pierre Nicolas, Villez-Sous-Bailleul (FR)

(73) Assignees: UNIVERSITE PIERRE ET MARIE CURIE (PARIS 6), Paris (FR); INSTITUT DE RECHERCHE POUR LE DEVELOPMENT, Marseilles (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 803 days.

(21) Appl. No.: 13/257,018

(22) PCT Filed: Mar. 18, 2010

(86) PCT No.: PCT/FR2010/050487
§ 371 (c)(1),
(2), (4) Date: Sep. 16, 2011

(87) PCT Pub. No.: WO2010/106293
PCT Pub. Date: Sep. 23, 2010

(65) Prior Publication Data
US 2012/0005790 A1    Jan. 5, 2012

(30) Foreign Application Priority Data

Mar. 19, 2009  (FR) ..................................... 09 51768

(51) Int. Cl.
*C07K 14/46* (2006.01)
*C12N 15/82* (2006.01)
(52) U.S. Cl.
CPC ......... *C07K 14/463* (2013.01); *C12N 15/8282* (2013.01); *C12N 15/8283* (2013.01)
(58) Field of Classification Search
None
See application file for complete search history.

(56) References Cited

U.S. PATENT DOCUMENTS 5,789,382 A * 8/1998 Wellstein .................. 514/9.1
5,916,872 A * 6/1999 Chang et al. .............. 514/2.6

OTHER PUBLICATIONS

Uniprot. Accession B3KYH4_PELSA. 2008.*
Abbassi et al. Solution structure and model membrane interaction sof temporins-SH, antimicrobial peptides from amphibian skin. A NMR spectroscopy and differential scanning calorimetry study. 2008. Biochemistry. 47:10513-10525.*
Wells, Biochemistry 29:8509-8517, 1990.*
Ngo et al., (The Protein Folding Problem and Tertiary Structure Prediction, K. Merz., and S. Le Grand (eds.) pp. 492-495,1994).*
Guo et al. (PNAS, 101: 9205-9210, 2004).*
Keskin et al. (Protein Science, 13:1043-1055, 2004).*
Thornton et al. (Nature structural Biology, structural genomics supplement, Nov. 2000).*
Abbassi et al (2008. Biochemistry. 47:10513-10525).*
Abbassi, F. et al. "Isolation, characterization and molecular cloning of new temporins from the skin of the North African ranid *Pelophylax saharica*" Peptides, 2008, pp. 1526-1533, vol. 29, XP-23902026.
Conlon, J. Michael. et al. "Strategies for transformation of naturally-occurring amphibian antimicrobial peptides into therapeutically valuable anti-infective agents" *Methods*, 2007, pp. 349-357, vol. 42, XP-002547419.
Dennison, S. R. et al. "Amphiphilic α-Helical Antimicrobial Peptides and Their Structure/Function Relationships" *Protein and Peptide Letters*, 2005, pp. 31-39, vol. 12, XP-008112284.
Abbassi, F. et al. "Solution Structure and Model Membrane Interactions of Temporins-SH, Antimicrobial Peptides from Amphibian Skin. A NMR Spectroscopy and Differential Scanning Calorimetry Study" *Biochemistry*, 2008, pp. 10513-10525, vol. 47, XP-002547417.
Conlon, J. Michael et al. "Antimicrobial peptides from the skins of North American frogs" *Biochimica et Biophysica Acta*, 2009, pp. 1556-1563, vol. 1788, No. 8, XP-002547418.
Giangaspero, A. et al. "Amphipathic α helical antimicrobial peptides" *Eur. J. Biochem*, 2001, pp. 5589-5600, vol. 268, XP-002547420.
Mangoni, M. L. "Temporins, anti-infective peptides with expanding properties" *Cell. Mol. Life Sci.*, 2006, pp. 1060-1069, vol. 63, XP-19419142.
Written Opinion in International Application No. PCT/FR2010/050487, Aug. 31, 2010, pp. 1-6.

* cited by examiner

*Primary Examiner* — Vinod Kumar
(74) *Attorney, Agent, or Firm* — Saliwanchik, Lloyd & Eisenschenk (57) ABSTRACT

The present invention relates to novel antimicrobial peptides, to pharmaceutical compositions comprising said peptides, and to the uses thereof, in particular as antimicrobial drugs, disinfectants, pesticides or preservatives. The present invention also relates to a transgenic plant expressing said novel peptides.

15 Claims, 3 Drawing Sheets

ANALOGS OF TEMPORIN-SHA AND USES THEREOF

CROSS-REFERENCE TO RELATED APPLICATION

This application is the U.S. national stage application of International Patent Application No. PCT/FR2010/050487, filed Mar. 18, 2010.

The present invention relates to novel antimicrobial peptides, to pharmaceutical compositions comprising said peptides and to the uses thereof, in particular as medicament or disinfectant. The present invention also relates to a transgenic plant expressing said novel peptides.

TECHNOLOGICAL BACKGROUND OF THE INVENTION

The evolution and spread of antibiotic resistance among bacteria is a major public health problem today, especially in the hospital setting with the emergence of multidrug resistant strains. Intensive research efforts have led to the development of new antibiotics effective against these resistant strains. Nevertheless, through use, mechanisms of resistance to these drugs emerge and limit their efficacy.

In view of this phenomenon, antimicrobial peptides (AMP) appear very promising for the design of new therapeutic agents. Cationic antimicrobial peptides are thought to be one of the key components of the innate immune system of pluricellular organisms which provides first-line defence against pathogens. The interest of these peptides lies on the one hand in their very broad spectrum of activity enabling in particular their use in the treatment of infections caused by multidrug resistant strains. Secondly, their mode of action is based on permeabilisation or rapid fragmentation of the microorganism membrane and is therefore unlikely to lead to the development of resistance mechanisms.

Antimicrobial peptides have been identified in plants, insects, amphibia and mammals. Amphibian skin represents a major source of antimicrobial peptides and every species of frog possesses its specific peptide repertoire generally composed of 10 to 15 AMP.

Frogs of the Ranidae family are very numerous and this family currently counts 16 genera and 338 species. These frogs synthesize and secrete a remarkable diversity of AMP which have been classified into 13 families (Conlon et al., 2008 and 2009). One such family, the temporins, comprises AMP of small size (generally between 10 and 14 residues) the sequences of which vary widely according to species. More than 60 members of the temporin family have been identified. These temporins have been isolated from several Rana species such as for example Rana temporaria (Simmaco et al., 1996), Rana esculenta (Simmaco et al., 1990), Rana japonica (Isaacson et al., 2002), Rana ornativentris (Kim et al., 2001) and Pelophylax (Rana) saharica (Abbassi et al., 2008).

Unlike the other 12 families of Ranidae peptides, the temporins lack the "Rana box" motif, a C-terminal heptapeptide domain cyclised by a disulphide bridge (Mangoni, 2006). Furthermore, the majority of temporins contain a single basic residue which confers a net charge of +2 at physiological pH.

Generally, the temporins are particularly active against Gram-positive bacteria and yeasts but they also exhibit antifungal properties (Rollins-Smith et al., 2003) and, for some, antiviral properties (Chinchar et al., 2004).

Recent studies on temporins A, B (Mangoni et al., 2006) and SHa (Abbassi et al., 2008) revealed that these peptides exhibit antiparasitic activity against protozoa belonging to the genus Leishmania, which are the causal agents of leishmaniasis. Apart from these temporins, very few AMP display antiparasitic activity: dermaseptins and polypeptide YY (also isolated from frog skin); indolicidin (isolated from bovine neutrophil granules); gomesin (isolated from the spider Acanthoscurria gomesiana); cecropin-melittin hybrids (obtained from insect molecules).

Leishmaniasis is an extremely widespread disease found across much of the world, essentially in India, South America, Africa and the Mediterranean basin. The parasite infects several million individuals every year. Depending on the Leishmania species, leishmaniasis can be of the cutaneous, mucocutaneous or visceral form. For example, visceral leishmaniasis, the most serious form and potentially fatal if untreated, is caused by two Leishmania species: Leishmania infantum and Leishmania donovani. The Leishmania life cycle comprises two successive morphological stages: the promastigote stage (free form in the gut of the insect vector, the sandfly) and the amastigote stage (intracellular form infecting the mononuclear phagocytes of the mammalian host).

The first-line therapy of leishmaniasis consists in the use of antimonials such as meglumine antimonate (Glucantime®) or soduim stibogluconate (Pentostam®). However, the efficacy of antimony is eroding due to the emergence of high level resistance which can reach 60% according to geographical location. Despite the availability of alternative treatments such as amphotericin B (Ambisome®) and miltefosin (Impavido®), there is an urgent need to find new drugs to fight this disease.

SUMMARY OF THE INVENTION

The invention aims to provide novel antimicrobial peptides, analogs of temporin-SHa and exhibiting increased antimicrobial activity, in particular against bacteria and the Leishmania parasite. Preferably, said novel peptides also have reduced hemolytic activity as compared to temporin-SHa.

The invention relates first of all to a peptide of a size comprised between 13 and 100 amino acids, exhibiting an antimicrobial activity and comprising the sequence F-L-$X_1$-$X_2$-I-V-$X_3$-M-L-$X_4$-K-L-F, (SEQ ID NO: 18), wherein $X_1$ is an amino acid selected from the group consisting of S, R, H and K, and $X_2$, $X_3$ and $X_4$, which are the same or different, are amino acids selected from the group consisting of G, R, H and K, and wherein, when $X_1$ represents S, at least one of the residues $X_2$, $X_3$ and $X_4$ is selected from the group consisting of R, H and K, and the functional derivatives and pharmaceutically acceptable salts of said peptide. Preferably, $X_1$ is an amino acid selected from the group consisting of R, H and K, and $X_2$, $X_3$ and $X_4$ represent G. Preferably, $X_1$ represents K, and $X_2$, $X_3$ and $X_4$ represent G.

In another aspect, the present invention relates to a nucleic acid coding for a peptide according to the invention.

The present invention also relates to an expression cassette comprising a nucleic acid according to the invention.

The present invention further relates to an expression vector comprising a nucleic acid encoding a peptide according to the invention.

In another aspect, the present invention relates to a host cell comprising a nucleic acid, a cassette or an expression vector according to the invention.

The present invention also relates to an antibody specifically binding to a peptide according to the invention.

In yet another aspect, the present invention relates to a pharmaceutical composition comprising at least one peptide according to the invention, and a pharmaceutically acceptable support and/or excipient.

The present invention further relates to a peptide according to the invention, as medicament. Preferably, the medicament is intended for treating an infection caused by a bacterium, a virus, a fungus or a parasite. Preferably, the parasite belongs to the genus *Leishmania*.

In still another aspect, the present invention relates to the use of a peptide according to the invention as disinfectant, preservative or pesticide.

In another aspect, the present invention relates to a medical device or implant comprising a body having at least one surface coated with or including a peptide according to the invention.

In a final aspect, the present invention relates to a transgenic plant comprising a nucleic acid, a cassette or an expression vector according to the invention, and able to express or expressing a peptide according to the invention.

DETAILED DESCRIPTION OF THE INVENTION

Temporin-SHa, formerly known as temporin-1Sa, was isolated from the skin of the North African frog *Pelophylax saharica* (Abbassi et al., 2008). This temporin is obtained by posttranslational maturation of a 50-residue precursor (Gen-Bank database number: CAO77282). This precursor has a highly conserved N-terminal domain containing the signal peptide and a region rich in acidic residues, as well as a hypervariable C-terminal domain containing the temporin-SHa progenitor sequence. In vivo, the mature form of temporin is obtained after i) proteolytic cleavage of the KR doublet which precedes the progenitor sequence, ii) elimination of the C-terminal K residue from the progenitor sequence by the action of a carboxypeptidase, and iii) amidation of the C-terminal residue of temporin by the C-terminal G residue of the progenitor sequence which serves as amide group donor (substrate of peptidyl-glycine α-amidating monooxygenase). The mature protein is a peptide of 13 amino acids in length and having the sequence F-L-S-G-I-V-G-M-L-G-K-L-F (SEQ ID No.1). Temporins are unstructured in aqueous solution but adopt an α helical structure in membrane-mimetic environments.

Said peptide exhibits antimicrobial activity against Gram-positive and Gram-negative bacteria, yeasts, and the parasite *Leishmania infantum* (Abbassi et al., 2008). The antiparasitic action of temporin-SHa occurs against both the promastigote and axenic amastigote forms of the parasite with an IC$_{50}$ of 18.1 μM and 22.8 μM, respectively.

The antimicrobial activity of antimicrobial peptides (AMP), and their cytolytic activities towards mammalian cells, reflect a subtle equilibrium between several parameters including net charge, hydrophobicity, helicity and amphipathy (Giangaspero et al., 2001; Yeaman et al., 2003; Dennison et al., 2005). These parameters are very closely linked and the mere substitution of an amino acid residue can induce a simultaneous modification of several physicochemical properties of the peptide.

The inventors have shown in a surprising manner that the substitution of one or more amino acids of the polar face of the a helix of temporin-SHa by a basic amino acid leads to an analog of said temporin having increased antimicrobial activity and reduced toxicity.

Herein, the terms "peptide", "oligopeptide", "polypeptide" and "protein" are employed interchangeably and refer to a chain of amino acids linked by peptide bonds, regardless of the number of amino acids forming said chain.

In the peptide sequences described herein, the amino acids are represented by their one-letter code according to the following nomenclature: C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan and Y: tyrosine.

The term "microbe" or "microbial" as employed herein refers to bacteria, fungi, yeasts, viruses and/or parasites.

The term "microbial infection" as employed herein refers to an infection caused by bacteria, fungi, yeasts, viruses and/or parasites.

The term "antimicrobial activity" as employed herein refers to an antibacterial, antiviral, antifungal and/or antiparasitic activity. Said activity may be evaluated by measuring different parameters such as IC$_{50}$, MIC or else MBC. "IC$_{50}$" or "half maximal inhibitory concentration" is the concentration of a substance needed to reduce the growth in vitro of a population of microorganisms by half. "MIC" or "minimum inhibitory concentration" is the lowest concentration of a substance that will totally inhibit microbial growth after 18 hours of incubation, generally at 37° C., in the presence of said substance. "MBC" or "minimum bactericidal concentration" is the lowest concentration of a substance that will kill 99.9% of microorganisms after 18 to 24 hours of contact with said substance.

The term "lethal concentration, 50%" or "LC$_{50}$" as employed herein refers to the concentration of substance required to kill half a cell population. LC$_{50}$ is a quantitative indicator of the toxicity of a substance. In particular, LC$_{50}$ is employed herein to evaluate the hemolytic activity of AMP and in this case corresponds to the concentration of peptide inducing hemolysis of half the erythrocyte population.

Figure 1:
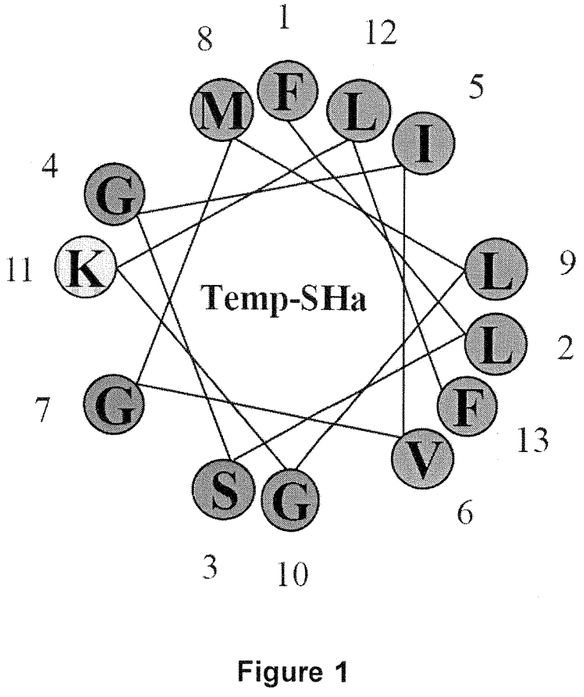
FIG. 1 represents a Schiffer-Edmunson projection of the α helix of temporin-SHa. Residues 4, 11, 7, 3 and 10 constitute the polar face of the helix. Residues 8, 1, 12, 5, 9, 2, 13 and 6 constitute the apolar face of the helix.

The present invention relates first of all to a peptide analog of temporin-SHa in which one or more amino acids of the polar face of the α helix are substituted by basic amino acids. According to the Schiffer-Edmunson projection of the α helix of temporin-SHa shown in FIG. 1, the amino acids constituting the polar face of said helix are residues 4, 11, 7, 3 and 10 of temporin-SHa, in particular such as presented in SEQ ID No. 1.

The present invention therefore relates to a peptide analog of temporin-SHa, exhibiting an antimicrobial activity and comprising the sequence F-L-X$_1$-X$_2$-I-V-X$_3$-M-L-X$_4$-K-L-F (SEQ ID No.18), wherein X$_1$ is an amino acid selected from the group consisting of S, R, H and K, and X$_2$, X$_3$ and X$_4$, which are the same or different, are amino acids selected from the group consisting of G, R, H and K, and wherein, when X1 represents S, at least one of the residues $X_2$, $X_3$ and $X_4$ is selected from the group consisting of R, H and K.

According to one embodiment, the peptide of the invention comprises a sequence selected from the group consisting of F-L-$X_1$-G-I-V-G-M-L-G-K-L-F (SEQ ID No.2);
F-L-S-$X_2$-I-V-G-M-L-G-K-L-F (SEQ ID No.3);
F-L-S-G-I-V-$X_3$-M-L-G-K-L-F (SEQ ID No.4);
F-L-S-G-I-V-G-M-L-$X_4$-K-L-F (SEQ ID No.5);
F-L-$X_1$-$X_2$-I-V-G-M-L-G-K-L-F (SEQ ID No.6);
F-L-$X_1$-G-I-V-$X_3$-M-L-G-K-L-F (SEQ ID No.7);
F-L-$X_1$-G-I-V-G-M-L-$X_4$-K-L-F (SEQ ID No.8);
F-L-S-$X_2$-I-V-$X_3$-M-L-G-K-L-F (SEQ ID No.9);
F-L-S-$X_2$-I-V-G-M-L-$X_4$-K-L-F (SEQ ID No.10);
F-L-S-G-I-V-$X_3$-M-L-$X_4$-K-L-F (SEQ ID No.11);
F-L-$X_1$-$X_2$-I-V-$X_3$-M-L-G-K-L-F (SEQ ID No.12);
F-L-$X_1$-$X_2$-I-V-G-M-L-$X_4$-K-L-F (SEQ ID No.13);
F-L-$X_1$-G-I-V-$X_3$-M-L-$X_4$-K-L-F (SEQ ID No.14);
F-L-S-$X_2$-I-V-$X_3$-M-L-$X_4$-K-L-F (SEQ ID No.15); and
F-L-$X_1$-$X_2$-I-V-$X_3$-M-L-$X_4$-K-L-F (SEQ ID No.16), in which $X_1$, $X_2$, $X_3$ and/or $X_4$ are basic amino acids selected from the group consisting of R, H and K. Preferably, $X_1$, $X_2$, $X_3$ and/or $X_4$ represent K. In a particular embodiment, $X_1$ represents K in SEQ ID Nos. 2 to 16.

According to one embodiment, the peptide has a size comprised between 13 and 100 amino acids, preferably between 13 and 30, 35, 40, 45 or 50 amino acids. According to another embodiment, the peptide has a size comprised between 13 and 15, 20 or 25 amino acids. In a particular embodiment, the peptide has a size of 13 amino acids.

The peptide according to the invention can be a precursor of a mature antimicrobial peptide. Said precursor then undergoes posttranslational modifications leading to the mature form of the AMP. It may thus comprise a translocation signal sequence and recognition and/or cleavage sites enabling it to undergo these posttranslational modifications. According to a particular embodiment, the peptide is a precursor of a mature antimicrobial peptide and comprises the sequence F-L-G-T-I-N-L-S-L-C-E-Q-E-R-D-A-D-E-E-E-R-D-E-P-N-E-S-N-V-E-V-E-K-R-F-L-$X_1$-$X_2$-I-V-$X_3$-M-L-$X_4$-K-L-F-G-K (SEQ ID No.17), where $X_1$ is an amino acid selected from the group consisting of S, R, H and K, and $X_2$, $X_3$ and $X_4$, which are the same or different, are amino acids selected from the group consisting of G, R, H and K, and where, when $X_1$ represents S, at least one of the residues $X_2$, $X_3$ and $X_4$ is selected from the group consisting of R, H and K.

The amino acids constituting the peptide of the invention may be in the L or D configuration, preferably the L configuration.

The peptide according to the invention may have a posttranslational modification and/or a chemical modification in particular a glycosylation, an amidation, an acylation, an acetylation or a methylation.

So as to enhance the bioavailability of the peptide by improving its resistance to peptidases, protective groups may be added to the C- and/or N-terminal ends. For example, the protective group at the N-terminal end may be an acylation or an acetylation and the protective group at the C-terminal end may be an amidation or an esterification. The action of proteases may also be blocked by the use of amino acids in the D configuration, cyclisation of the peptide by formation of disulphide bridges, lactam rings or bonds between the C- and N-terminal ends. The peptide of the invention may also comprise pseudo-peptide bonds replacing the "classical" CONH peptide bonds and conferring increased resistance to peptidases, such as CHOH—CH2, NHCO, CH2—O, CH2CH2, CO—CH2, N—N, CH=CH, CH2NH, and CH2—S. Preferably, the peptide according to the invention has an amidation at its C-terminal end.

The peptide according to the invention may comprise one or more amino acids which are rare amino acids in particular hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid; or synthetic amino acids in particular ornithine, norleucine, norvaline and cyclohexyl-alanine.

The invention also encompasses functional derivatives of a peptide according to the invention such as described above. The term "functional derivative" as employed herein refers to peptides having substantially the same amino acid sequence, substantially the same helicoid structure and substantially the same antimicrobial activity. Said functional derivatives may, for example, be retropeptides, retro-inverso peptides, peptides having conservative substitutions and peptides whose side chain of one or more amino acids is substituted by groups that do not modify the antimicrobial activity of the peptide of the invention. The term "conservative substitution" as employed herein refers to a substitution of an amino acid residue by another which has similar chemical or physical properties (size, charge or polarity). As an example, isoleucine, leucine, alanine, valine, phenylalanine, proline and glycine may be mutually conservatively substituted, just like lysine, histidine and arginine or serine, tyrosine and threonine or cysteine and methionine or asparagine, glutamine and tryptophan or aspartic acid and glutamic acid. The term "functional derivative" also refers to a peptide according to the invention whose sequence is shortened by 1, 2, 3 or 4 amino acids at the C-terminal and/or N-terminal end.

The invention also encompasses the pharmaceutically acceptable salts of a peptide according to the invention. Pharmaceutically acceptable salts may, for example, be salts of pharmaceutically acceptable mineral acids such as hydrochloric acid, hydrobromic acid, sulphuric acid and phosphoric acid; salts of pharmaceutically acceptable organic acids such as acetic acid, citric acid, maleic acid, malic acid, succinic acid, ascorbic acid and tartaric acid; salts of pharmaceutically acceptable mineral bases such as salts of sodium, potassium, calcium, magnesium or ammonium; or salts of organic bases which contain a salifiable nitrogen, commonly used in pharmaceutical technique. The methods for preparing said salts are well known to one of skill in the art.

The peptide according to the invention may be obtained by classical chemical synthesis (in solid phase or homogeneous liquid phase) or by enzymatic synthesis (Kullman et al., 1987). It may also be obtained by the method consisting in culturing a host cell, such as described hereinafter, comprising a transgene coding for the peptide and expressing said peptide, and extracting said peptide from said host cells or from the culture medium into which the peptide was secreted.

The peptide according to the invention exhibits an antimicrobial activity. In an advantageous manner, said activity is superior to that of temporin-SHa against at least one bacterial, viral, fungal or parasitic strain. According to one embodiment, the peptide according to the invention has greater antimicrobial activity than temporin-SHa against bacteria and more specifically against Gram-negative bacteria such as *Escherichia coli* and *Pseudomonas aeruginosa*. According to a particular embodiment, the peptide of the invention has an MIC less than 10 µM for *Pseudomonas aeruginosa*. According to a preferred embodiment, the peptide of the invention has greater antimicrobial activity than temporin-SHa against parasites, in particular against the parasites *Leishmania infantum, Leishmania donovani, Leishmania amazonensis, Leishmania major, Leishmania mexicana, Leishmania panamensis, Leishmania tropica, Leishmania braziliensis, Leishmania guyanensis* and/or *Leishmania peruviana*, more particularly against the parasites *Leishmania infantum, Leishmania major, Leishmania tropica* and/or *Leishmania braziliensis*, and in an especially preferred manner against the parasite *Leishmania infantum*. According to a particular embodiment, the peptide according to the invention has an $IC_{50}$ less than 15 µM for the promastigote form of the *Leishmania infantum* parasite.

According to a preferred embodiment, the peptide according to the invention has a hemolytic activity less than that of temporin-SHa. According to a particular embodiment, the peptide according to the invention has an $LC_{50}$ for erythrocytes greater than 30 µM.

The present invention also relates to a nucleic acid coding for a peptide according to the invention.

In the spirit of the invention, "nucleic acid" is understood to mean any molecule based on DNA or RNA. These may be synthetic or semi-synthetic, recombinant molecules, possibly amplified or cloned into vectors, chemically modified, comprising non-natural bases or modified nucleotides comprising for example a modified bond, a modified purine or pyrimidine base, or a modified sugar.

The nucleic acid according to the invention may be in the form of DNA and/or RNA, single stranded or double stranded. According to a preferred embodiment, the nucleic acid is an isolated DNA molecule, synthesized by recombinant techniques well known to one of skill in the art.

The nucleic acid according to the invention may be deduced from the sequence of the peptide according to the invention and codon usage may be adapted according to the host cell in which the nucleic acid shall be transcribed. These steps may be carried out according to methods well known to one of skill in the art and some of which are described in the reference manual Sambrook et al. (Sambrook et al., 2001).

The present invention further relates to an expression cassette comprising a nucleic acid according to the invention operably linked to the sequences required for its expression. In particular, the nucleic acid may be under the control of a promoter allowing its expression in a host cell. Generally, an expression cassette is constituted of or comprises a promoter allowing initiation of transcription, a nucleic acid according to the invention, and a transcription terminator. The term "expression cassette" denotes a nucleic acid construct comprising a coding region and a regulatory region, operably linked. The expression "operably linked" indicates that the elements are combined in such a way that the expression of the coding sequence (the gene of interest) and/or the targeting of the encoded peptide are under the control of the transcriptional promoter and/or signal peptide. Typically, the promoter sequence is placed upstream of the gene of interest, at a distance therefrom which is compatible with the control of expression. Likewise, the sequence of the signal peptide is generally fused upstream of the sequence of the gene of interest, and in the same reading frame with the latter, and downstream of any promoter. Spacer sequences may be present, between the regulatory elements and the gene, as long as they do not prevent expression and/or targeting. In a preferred embodiment, said expression cassette comprises at least one "enhancer" activating sequence operably linked to the promoter.

The present invention also relates to an expression vector comprising a nucleic acid or an expression cassette according to the invention. Said expression vector may be used to transform a host cell and enable the expression of the nucleic acid of the invention in said cell.

The vector may be a DNA or an RNA, circular or not, single- or double-stranded. Advantageously it is selected from among a plasmid, a phage, a phagemid, a virus, a cosmid and an artificial chromosome.

Advantageously, the expression vector comprises regulatory elements allowing the expression of the nucleic acid according to the invention. These elements may contain for example transcriptional promoters, transcriptional activators, terminator sequences, initiation and termination codons. The methods for selecting said elements according to the host cell in which expression is desired, are well known to one of skill in the art.

The vector may also contain elements enabling its selection in the host cell such as, for example, an antibiotic resistance gene or a selectable gene providing complementation of the respective gene deleted from the host cell genome. Such elements are well known to one of skill in the art and extensively described in the literature.

When the host cell to be transformed is a plant cell, the expression vector is preferably a plant vector. Examples of plant vectors are described in the literature, including in particular the T-DNA plasmids of *A. tumefaciens* pBIN19 (Bevan, 1984), pPZP100 (Hajdukewicz et al., 1994), the pCAMBIA series (R. Jefferson, CAMBIA, Australia). The vectors of the invention may additionally comprise an origin of replication and/or a selectable marker gene and/or a plant recombination sequence.

The vectors may be constructed by the classical techniques of molecular biology, well known to one of skill in the art.

The present invention relates to the use of a nucleic acid, an expression cassette or an expression vector according to the invention to transform or transfect a cell. The host cell may be transformed/transfected in a transient or stable manner and the nucleic acid, cassette or vector may be contained in the cell in the form of an episome or in chromosomal form.

The present invention relates to a host cell comprising a nucleic acid, a cassette or an expression vector according to the invention.

According to one embodiment, the host cell is a microorganism, preferably a bacterium or a yeast.

According to another embodiment, the host cell is an animal cell, for example a mammalian cell such as COS or CHO cells (U.S. Pat. Nos. 4,889,803; 5,047,335). In a particular embodiment, the cell is non-human and non-embryonic.

According to yet another embodiment, the host cell is a plant cell. The term "plant cell" as employed herein refers to any cell coming from a plant and which may constitute undifferentiated tissues such as calluses, and differentiated tissues such as embryos, plant parts, plants or seeds.

The present invention also relates to a method for producing an antimicrobial peptide according to the invention comprising transforming or transfecting a cell with a nucleic acid, an expression cassette or an expression vector according to the invention; culturing the transfected/transformed cell; and recovering the peptide produced by said cell. Methods for producing recombinant peptides are well known to one of skill in the art. For example, one may cite the specific methods described in WO 01/70968 for a production in an immortalized human cell line, WO 2005/123928 for a production in a plant and US 2005-229261 for a production in the milk of a transgenic animal.

The present invention also relates to a method for producing an antimicrobial peptide according to the invention comprising inserting a nucleic acid, a cassette or an expression vector according to the invention in an in vitro expression system also called acellular and recovering the peptide produced by said system. Many in vitro or acellular expression systems are commercially available and the use of said systems is well known to one of skill in the art.

The present invention additionally relates to a peptide according to the invention as medicament, in particular as medicament for treating a microbial infection, namely an infection due to bacteria, a virus, a fungus or a parasite. It also relates to a nucleic acid, a cassette or a vector according to the invention as medicament. The medicament may be intended for pharmaceutical or veterinary use.

According to a particular embodiment, the infection is an infection due to a parasite, preferably from the genus *Leishmania*. The infection by a parasite may be a cutaneous leishmaniasis, a mucocutaneous leishmaniasis or a visceral leishmaniasis. The parasite may be selected from the group consisting of *Leishmania aethiopica, Leishmania amazonensis, Leishmania arabica, Leishmania aristedes, Leishmania braziliensis, Leishmania infantum, Leishmania colombiensis, Leishmania deanei, Leishmania donovani, Leishmania enriettii, Leishmania equatorensis, Leishmania forattinii, Leishmania garnhami, Leishmania gerbili, Leishmania guyanensis, Leishmania herreri, Leishmania hertigi, Leishmania lainsoni, Leishmania major, Leishmania mexicana, Leishmania naiffi, Leishmania panamensis, Leishmania peruviana, Leishmania pifanoi, Leishmania shawi, Leishmania turanica, Leishmania tropica* and *Leishmania venezuelensis*. Preferably, the parasite is selected from the group consisting of *Leishmania infantum, Leishmania donovani, Leishmania mexicana, Leishmania amazonensis, Leishmania major, Leishmania tropica, Leishmania braziliensis, Leishmania guyanensis, Leishmania panamensis* and *Leishmania peruviana*. In a particularly preferred manner, the parasite is selected from the group consisting of *Leishmania infantum, Leishmania major, Leishmania tropica* and *Leishmania braziliensis*. In a most particularly preferred manner, the infection is an infection by the parasite *Leishmania infantum*.

The infection may also be an infection due to a parasite from the genus *Trypanosoma*. The parasite may be selected from the group consisting of *Trypanosoma avium, Trypanosoma brucei, Trypanosoma cruzi, Trypanosoma congolense, Trypanosoma equinum, Trypanosoma equiperdum, Trypanosoma evansi, Trypanosoma lewisi, Trypanosoma melophagium, Trypanosoma percae, Trypanosoma rangeli, Trypanosoma rotatorium, Trypanosoma simiae, Trypanosoma suis, Trypanosoma theileri, Trypanosoma triglae* and *Trypanosoma vivax*. Preferably, the parasite is selected from the group consisting of *Trypanosoma brucei, Trypanosoma cruzi* and *Trypanosoma congolense*.

The present invention relates to a peptide according to the invention as antimicrobial agent. The present invention also relates to a nucleic acid, a cassette or a vector according to the invention as antimicrobial agent.

The present invention relates to a peptide according to the invention as immune system stimulating agent, particularly during a microbial infection. The invention also relates to a nucleic acid, a cassette or a vector according to the invention as immune system stimulating agent. According to a particular embodiment of the invention, the peptide according to the invention has chemotactic properties. The peptide induces the recruitment of immune cells to the site of the infection and increases the effectiveness of the immune response to infections.

The present invention also relates to a pharmaceutical composition comprising at least one peptide according to the invention and a pharmaceutically acceptable support and/or excipient. The present invention also relates to a pharmaceutical composition comprising at least one nucleic acid, cassette or vector according to the invention and a pharmaceutically acceptable support and/or excipient.

The pharmaceutically acceptable excipients and supports that can be used in the composition according to the invention are well known to one of skill in the art (Remington's Pharmaceutical Sciences, 18$^{th}$ edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3$^{rd}$ edition, A. Kibbe, Ed., Pharmaceutical Press[2000]) and comprise in particular physiological saline solutions and phosphate buffers.

The pharmaceutical composition according to the invention may be suitable for oral, sublingual, cutaneous, subcutaneous, intramuscular, intravenous, topical, local, intratracheal, intranasal, transdermal, rectal, intraocular or intraauricular administration. Preferably, the pharmaceutical composition according to the invention is suitable for cutaneous, oral, intramuscular, intravenous, transdermal or subcutaneous administration. According to a particular embodiment, the pharmaceutical composition according to the invention is suitable for topical administration. The pharmaceutical composition according to the invention may be in the form of tablets, capsules, soft capsules, granulates, suspensions, emulsions, solutions, gels, pastes, ointments, creams, plasters, potions, suppositories, enemas, injectables, implants, patches, sprays or aerosols.

According to one embodiment, the composition according to the invention comprises from 1 to 2000 mg of peptide according to the invention. Preferably, the composition according to the invention comprises from 50 to 100, 150, 200, 250, 500, 750, 1000 or 1500 mg of peptide according to the invention.

The composition according to the invention may further comprise additional active substances, such as other antimicrobial agents, in particular antimicrobial peptides or antibiotics. The composition may also additionally comprise substances that can potentiate the activity of the peptide according to the invention.

The present invention relates to the use of a peptide according to the invention for preparing a medicament for treating a microbial infection. The invention also relates to the use of a nucleic acid, a cassette or a vector according to the invention for preparing a medicament for treating a microbial infection.

The present invention relates to a peptide according to the invention for use in the treatment of a microbial infection. The present invention also relates to a nucleic acid, a cassette or a vector according to the invention for use in the treatment of a microbial infection.

The treatment may be curative or preventive.

The subject to be treated is an animal, preferably a mammal. According to a particular embodiment, the subject to be treated is a human.

The present invention also relates to a method for treating a microbial infection comprising administering a therapeutically effective dose of a peptide, a nucleic acid, a cassette or a vector according to the invention.

The term "therapeutically effective dose" as employed herein refers to the amount of peptide, nucleic acid, cassette or vector according to the invention required in order to observe an antimicrobial activity on the bacterium, virus, fungus or parasite responsible for the infection. The amount of peptide, nucleic acid, cassette or vector according to the invention to be administered and the duration of the treatment are determined by the one of the art according to the physiological condition of the subject to be treated, the pathogenic agent and the antimicrobial activity of the peptide towards said pathogenic agent.

In a particular embodiment, the microbial infection to be treated is leishmaniasis.

An effective dose of the peptide of the invention may comprise, but is not limited to, between approximately 1 and 40 mg/kg of body weight. The frequency of administration may be for example every 4 to 24 hours, preferably every 8 to 12 hours. The duration of treatment may be for example from 1 to 30 days, preferably from 10 to 20 days, and most preferably from 5 to 10 days.

The present invention also relates to the use of the peptide according to the invention as preservative, disinfectant or pesticide.

Food products may be treated with a peptide according to the invention in order to eliminate or prevent the risk of infection by microorganisms and thereby improve their conservation. In this case the peptide is used as preservative.

The peptide according to the invention may be used as pesticide. In this case the peptide is used to prevent or treat infections of plants by phytopathogens.

The peptide according to the invention may also be used as disinfectant. The term "disinfectant" refers to an antimicrobial activity of the peptide on a surface (for example, walls, doors, medical equipment), a liquid (for example, water) or a gas (for example, an anesthetic gas).

Biofilms are responsible for approximately 60% of nosocomial infections. They are essentially due to microbial colonisation of implanted biomaterials. Eradication of a bacterial biotilm is a major clinical problem considering that antibiotics normally active on bacteria in planktonic state often turn out to be much less effective against structures organized into a biofilm. The effect of the antimicrobial peptides on this type of biofilm has been demonstrated in previous studies carried out with temporin-A (Cirioni et al., 2003).

According to one embodiment, the peptide according to the invention is used for elimination of bacterial biofilms. According to a preferred embodiment, the peptide according to the invention is used in particular for disinfecting surgical or prosthetic equipment.

The present invention also relates to a medical device or implant comprising a body having at least one surface coated with or including a peptide according to the invention. In particular, the surface may be coated with a peptide at a density of 0.4 to 300 mg/cm$^2$. The peptide may be combined with another active molecule, preferably an antibiotic. The implant may be a vascular implant.

The present invention also relates to a method for preparing a medical device or implant comprising applying a coating of peptide according to the invention, or placing in contact, with at least one surface of the device or implant. This type of medical device or implant and the uses and methods of preparation thereof are described for example in patent application WO 2005/006938.

The present invention relates to a food composition comprising at least one peptide according to the invention.

The present invention also relates to an agrochemical composition comprising at least one peptide according to the invention.

The present invention relates to a transgenic plant comprising a nucleic acid, a cassette or an expression vector according to the invention, and able to express or expressing a peptide according to the invention.

Introduction of nucleic acids, cassettes or expression vectors of the invention in a cell or a plant tissue, including a seed or plant, may be carried out by any method known to one of skill in the art. Plant transgenesis methods are well known in the field, and comprise for example the use of the bacterium *Agrobacterium tumefaciens* (Hooykaa and Schilperoort, 1992), electroporation, conjugative transfer, biolistic techniques (Russel et al., 1992) or microinjection into plant embryos or protoplasts. Other plant transgenesis techniques are well known, or other procotols implementing the above techniques are described in the prior art (Siemens and Schieder, 1996) and may be applied to the present invention. The transgenic plant according to the invention may be obtained in particular according to the method described in patent application WO 00/055337.

The transgenic plant may belong to any plant species. It may be monocotyledonous or dicotyledonous. More particularly, the transgenic plant of the invention is a cultured plant intended or not for animal or human food or on which the sandfly, the insect vector of leishmaniasis, alights to feed, such as maize, wheat, rapeseed, soy, alfalfa, flax, rice, sugar cane, beet, tobacco, cotton, sunflower, tomato, cabbage, carrot, potato, or fruit trees such as the lemon tree, apple tree, apricot tree, peach tree and hazel tree, or plants identified to date as sugar meal sources for sandflies such as *Ricinus communis, Capparis spinosa, Solanum jasminoides, Solanum luteum* or *Bougainvillea glabra.*

According to one embodiment, the expression of the peptide according to the invention allows the transgenic plant to have increased resistance to pathogens, and more particularly to phytopathogens. The use of such transgenic plant makes it possible to considerably reduce the spraying or application of pesticides on the crops, and thereby to minimize the harmful environmental effects of these products.

According to another embodiment, the transgenic plant expresses a peptide according to the invention which is administered to an animal including sandflies or a human by ingestion of said plant or its juices. In this case, the peptide does not necessarily have an effect on the phytopathogens but displays antimicrobial activity against one or more pathogens of the animal including the *leishmania* parasites present in the gut of the sandfly vectors of human and animal leishmaniasis or the human to which it is administered. The transgenic plants on which the sandflies take their sugar meal, directly deliver into the gut of the insect vector an antimicrobial peptide of the invention which kills the parasite eventually present in the insect vector directly or by blocking its development by killing the bacteria of the intestinal flora of the insect vector, required for parasite differentiation or multiplication. Transgenic plants in fact constitute an effective means of indirect control of transmission of leishmaniasis.

The present invention relates to an antibody specific of the peptide according to the invention. The term "antibody" as employed herein refers in particular to polyclonal or monoclonal antibodies, fragments thereof (for example the fragments F (ab) '2, F (ab)), single chain antibodies or minibody or else any polypeptide comprising a domain of the initial antibody recognizing the peptide of the invention, particularly CDRs (complementarity determining regions). For example these are chimeric, humanised or human antibodies. Monoclonal antibodies may be prepared from hybridomas according to methods well known to one of skill in the art. The different methods for preparing antibodies are well known to one of skill in the art.

The present invention also relates to the use of an antibody according to the invention for detecting a peptide according to the invention. It further relates to the use of an antibody according to the invention for making quantitative measurements of a peptide according to the invention, in particular for immunological assays. Said measurements can allow in particular a determination of the expression of the peptide of the invention in a host cell or a transgenic plant according to the invention.

All the references cited in this description are incorporated by reference in the present application. Other features and advantages of the invention will become clearer in the following examples which are given for purposes of illustration and not by way of limitation.

EXAMPLES

Materials and Methods
Solid Phase Peptide Synthesis

Solid phase peptide synthesis was carried out with the aid of an automated peptide synthesizer (Applied Biosystems 433A) according to the protocol described by Vanhoye et al. (Vanhoye et al., 2004), and by using Fmoc-protected amino acids (Novabiochem, Switzerland) and Rink amide MBHA resin (Senn Chemicals, Switzerland).

The synthetic peptides were purified by RP-HPLC on a semipreparative C18 column (Waters RCM compact preparative cartridge module, 300 Å, 25×100 mm), using a 0-60% acetonitrile gradient (1%/min) at a flow rate of 8 ml/min. The homogeneity and identity of the synthetic peptides were assessed by analytical RP-HPLC (Symmetry C18 column, 5 μm, 4.6×250 mm, Waters—flow rate: 0.75 ml/min) and MALDI-TOF mass spectrometry (Voyager DE-PRO, Applied Biosystems).

Tests of Antibacterial Activity

The following strains were used for the antibacterial activity tests: *Escherichia coli* (ATCC 25922 and ATCC 35218), *Staphylococcus aureus* (ATCC 25923), *Enterococcus faecalis* (ATCC 29212), *Bacillus megaterium* and *Pseudomonas aeruginosa* (ATCC 27853).

For each strain, a standard inoculum of $10^5$ to $10^6$ bacteria/mL (exponential growth phase) was prepared. To this end, a colony isolated on LB agar previously inoculated with one of the strains was cultured in 10 mL of LB broth medium. Liquid cultures were then incubated for 2 to 3 hrs at 37° C. with shaking for the bacteria to reach exponential growth phase. Each bacterial suspension was diluted in LB medium to an $OD_{630nm}$ of 0.01 which corresponds to a concentration of $10^5$-$10^6$ cfu/mL (cfu: colony forming unit).

The minimum inhibitory concentration (MIC) of each peptide was determined by a test of growth inhibition in broth medium. MIC is defined as the lowest concentration of peptide able to inhibit the growth of the bacterial strain tested after 18 hrs of incubation at 37° C. The test was performed in a sterile 96-well microtiter plate. A series of increasing concentrations of each peptide (1 to 400 μM) was first prepared in sterile MilliQ water containing 5% dimethyl sulphoxide (DMSO). DMSO facilitates peptide solubilisation and has no antimicrobial activity at the concentration used. 50 μL of peptide were aliquoted into each well with 50 μL of bacterial suspension ($10^5$-$10^6$ cfu/mL). The microtiter plate was then incubated for 18 hrs at 37° C. with shaking. Bacterial growth was determined by measuring OD at 630 nm (turbidity) on a plate reader. Tests were carried out in triplicate for each peptide concentration.

The growth inhibition negative control was obtained by replacing the solution containing the peptide with 50 μL of sterile MilliQ water containing 5% DMSO. The positive control allowing the complete inhibition of bacterial strains was obtained by replacing the solution containing the peptide with 50 μL of 0.7% formaldehyde.

Tests of Antifungal Activity

Three yeast strains were used: *Saccharomyces cerevisiae*, *Candida albicans* (ATCC 90028), *Candida parapsilosis* (ATCC 22019). These strains were first grown on YPD agar for a minimum of 48 hrs. Yeast suspensions were then prepared, exactly as for bacteria, and adjusted to $10^5$-$10^6$ cfu/mL in YPD broth medium.

The antifungal activity test corresponds to the growth inhibition test in broth medium used for the bacteria (see above) in which LB medium was replaced by YPD medium. Fungal strains were incubated at 30° C.

Hemolytic Tests

The hemolytic activity of the antimicrobial peptides was assessed using human erythrocytes from healthy donors. Red blood cell hemolysis is manifested by the release into the reaction medium of hemoglobin, the concentration of which is determined spectrophotometrically at 450 nm.

Red blood cells were separated from plasma and white blood cells by centrifugation of human blood (900 g, 10 min). The pellet containing red blood cells was washed three times with PBS buffer, pH 7.4. After counting on a Malassez cell, a stock solution of $2.10^7$ red blood cells/mL was prepared in the same buffer. A series of concentrations of the peptides to be tested was prepared (1 to 200 μM).

The test was carried out as follows: 100 μL of the different peptide concentrations were added to 100 μL of the red blood cell suspension. After 1 hr of incubation at 37° C. followed by centrifugation (12,000 g, 15 sec), absorbance of the supernatant was measured at 450 nm. The negative control for this test (0% hemolysis) contained 100 μL of PBS buffer in place of the peptide solution. The positive control (100% hemolysis) contained 100 μL of 0.1% Triton in place of the peptide solution.

The $LC_{50}$ value obtained is the mean of three experiments carried out in triplicate and corresponds to the peptide concentration inducing hemolysis of 50% of the cells.

Tests of Anti-Leishmania Activity

The antiparasitic activity of the peptides was evaluated on two forms of the parasite *Leishmania infantum*, the promastigote form and the amastigote form.

The tests of anti-*Leishmania* activity were carried out with a *Leishmania infantum* cell line αNEO-αLUC This cell line was obtained by transforming *Leishmania infantum* strain MHOM/MA/67/ITMAP-263 with the vector pGM αNEO-αLUC containing the luciferase reporter gene (LUC) and the neomycin resistance gene (NEO) such as described in Roy et al. (2000). It was maintained in culture in its two forms, promastigote and amastigote.

Parasite Culture:

*Leishmania infantum* promastigotes were maintained at 26° C. by one or two weekly passages depending on the number of parasites in the inoculum, in SDM 79 medium supplemented with 10 to 20% decomplemented foetal calf serum and 5 mg/mL porcine haemin and in the presence of 100 U/mL penicillin and 100 μg/mL streptomycin (Brun &

Shonenberger, 1979). Starting from an inoculum of $10^5$ cells/mL in logarithmic growth phase, the promastigotes reached a cell density of 2 to $3 \times 10^8$ parasites/mL in stationary phase after 7 days of culture in 25 cm$^2$ culture flasks. Cell densities were determined by flow cytometry in the presence of propidium iodide on a Facscan cytometer (Excalibur, Becton-Dickinson, Ivry, France).

Axenic amastigotes were obtained by differentiation of promastigotes at 37° C.±0.1° C. (H$_2$O saturation, 5% CO$_2$), cultured in MAA medium supplemented with 20% decomplemented foetal calf serum and 12.5 mg/mL porcine haemin, in the presence of 100 U/mL penicillin and 100 µg/mL streptomycin (Sereno and Lemesre, 1997). Starting from an inoculum of $5 \times 10^5$ cells/mL in logarithmic growth phase, the amastigotes reached a cell density of 2 to $3 \times 10^8$ parasites/mL in stationary phase after 7 day's of culture in 25 cm$^2$ culture flasks. Observation of the axenic amastigotes under a microscopic showed homogeneous shapes (round to ovoid) without visible flagella and immobile. The axenic amastigotes from various *Leishmania* species have the same ultrastructural, biological, biochemical and immunological properties as intracellular amastigotes. Cell densities were also determined by flow cytometry according to the same procedure and with the same parameters used for the promastigotes.

Tests of Anti-Leishmania Activity on Axenic Amastigotes:

A suspension of axenic amastigotes from the *Leishmania infantum* cell line transfected with the αNEO-αLUC cassette in exponential growth phase and with more than 90% viability was adjusted to a density of $1.25 \times 10^6$ parasites/mL in MAA/20 medium. Five-fold concentrated solutions of antimicrobial peptides were also prepared in this medium (300 to 4.7 µM).

To perform the test, the axenic amastigote suspension was aliquoted at 80 µL per well into a microtiter plate (corresponding to $10^5$ parasites/well) to which 20 µL of each peptide solution were added (60 to 0.94 µM final concentration) (for a final parasite density of $10^6$ parasites/mL). The plate was then incubated for 72 hours at 37° C. For the negative control the peptide solution was replaced by 20 µL of MAA/20 medium. The positive control was carried out with 20 µL of the solution with the highest peptide concentration. Experiments were done in triplicate for each peptide concentration. After 72 hrs, 50 µL of lysis buffer (Steady Glo, Promega) were added to each well. After a 5-min incubation at room temperature, cell lysis was checked under a microscope.

Emitted luminescence was measured with a luminescence plate reader (Victor, PerkinElmer). It is proportional to the number of viable parasites in the medium.

The percentage growth was calculated according to the following formula:

% growth=$[(L \text{ mean}-bgd)_{peptide} \times 100]/(L \text{ mean}-bgd)_{control}$ where L mean: mean luminescence and bgd: background.

The concentration inhibiting amastigote growth by 50% (IC$_{50}$) was determined.

Tests of Anti-*Leishmania* Activity on Promastigotes:

As for the amastigote tests, 80 µL of a promastigote suspension ($10^5$ parasites/well) were aliquoted into each well of a microtiter plate together with 20 µL of peptide solution (60 to 0.94 µM final concentration). Negative and positive controls were carried out according to the same protocol as for the tests of anti-*Leishmania* activity on amastigotes. Experiments were done in triplicate for each peptide concentration.

After 72 hours of incubation at 26° C., 50 µL of Steady Glo lysis buffer (Promega) were added to each well. After a 5-min incubation at room temperature, cell lysis was checked under a microscope. Emitted luminescence was measured and the percentage growth was calculated as above. The concentration inhibiting promastigote growth by 50% (IC$_{50}$) was determined.

Cytotoxicity Tests on Monocytes:

The cytotoxic activity of the antimicrobial peptides was determined on a human monocyte cell line THP-1. Cells were cultured in RPMI medium (10% FCS, 100 U/mL penicillin, 100 µg/mL streptomycin) until reaching exponential growth phase. After counting in a Thoma counting chamber, cell density was adjusted to $6.25 \times 10^5$ cells/mL in RPMI 1640 medium. Five-fold concentrated solutions of antimicrobial peptides were prepared in this RPMI medium (300 to 4.7 µM).

Monocytes were aliquoted at 80 µL of cell suspension per well (corresponding to $5 \times 10^4$ monocytes/well or $5 \times 10^5$ cells/mL final) and mixed with 20 µL of peptide solution (60 to 0.94 µM final concentration). Negative and positive controls were carried out according to the same protocol as for the tests of anti-*Leishmania* activity. Experiments were done in triplicate for each peptide concentration. Cells were incubated at 37° C., in a 5% CO$_2$ atmosphere for 72 hrs.

After 72 hours, the number of viable THP-1 cells was calculated indirectly by the MTT test (Mosmann, 1983). MTT (or 3-(4,5-dimethylthiazol-2-yl)-2,5-diphenyl-tetrazolium bromide), which is yellow in colour, is reduced to formazan, which is blue in colour, by the action of succinate-tetrazolium reductase which is present in the mitochondrial respiratory chain of metabolically active cells. Blue formazan can be detected spectrophotometrically at 570 nm.

A 10 mg/mL MTT solution in PBS buffer (pH 7.4), filtered on a 0.45 µm filter, was aliquoted at 10 µL per well. Plates were then incubated for 4 hrs at 37° C. The enzymatic reaction was stopped by adding 100 µl of a 50% isopropanol/10% SDS mixture and the plates were then incubated at room temperature for 30 min with shaking. The OD at 570 nm of each well was then measured (Victor plate reader, PerkinElmer) to calculate the IC$_{50}$.

Results

Antibacterial, Antifungal and Hemolytic Activities of Temporin-SHa and the Analog [K$^3$]temporin-SHa The antimicrobial activity of temporin-SHa (SEQ ID No.1) and the analog [K$^3$]temporin-SHa (SEQ ID No.19) was evaluated on different Gram-positive and Gram-negative bacterial reference strains and on fungal strains.

The hemolytic activity of these two peptides was also evaluated. Minimum inhibitory concentrations (MIC) and lethal concentrations 50 (LC$_{50}$) are shown in Table 1 below.

TABLE 1

Antimicrobial and hemolytic activities of temporin-SHa and the analog [K$^3$]temporin-SHa

| | MIC (µM) | |
|---|---|---|
| | Temp-SHa | [K$^3$] Temp-SHa |
| Gram-negative | | |
| *Escherichia coli* (ATCC 25922) | 10 | 3 |
| *Escherichia coli* (ATCC 35218) | 10 | 3 |
| *Escherichia coli* ML-35p | 6.25 | 3 |
| *Pseudomonas aeruginosa* (ATCC 27853) | 31.25 | 3 |

TABLE 1-continued

Antimicrobial and hemolytic activities of temporin-SHa and the analog [K³]temporin-SHa

| | MIC (µM) | |
|---|---|---|
| | Temp-SHa | [K³] Temp-SHa |
| Gram-positive | | |
| Staphylococcus aureus (ATCC 25923) | 3 | 3 |
| Enterococcus faecalis (ATCC 29212) | 10 | 10 |
| Bacillus megaterium | 2.5 | 1.5 |
| Yeasts | | |
| Candida albicans (ATCC 90028) | 15 | 12.5 |
| Candida parapsilosis (ATCC 22019) | 31.25 | 12.5-6.25 |
| Saccharomyces cerevisiae | 7.9 | 6.25 |
| $LC_{50}$ erythrocytes (µM) | 25 | 50 |

These results demonstrate that the antimicrobial activity of the analog [K³]temporin-SHa is remarkably higher than that of temporin-SHa, particularly against Gram-negative strains (MIC of 3 µM for all strains tested) and yeasts.

It is notable that the antibacterial activity of the analog [K³]temporin-SHa against *Pseudomonas aeruginosa* is 10 times higher than that of temporin-SHa. This finding is especially noteworthy considering that this strain is resistant to the majority of temporins.

Moreover, the increased antimicrobial potency of the analog [K³]temporin-SHa is accompanied by a twofold decrease in hemolytic activity as compared with that of temporin-SHa.

Anti-*Leishmania* Activity of Temporin-SHa and the Analog [K³]Temporin-SHa

The anti-*Leishmania* activity of the two temporins was evaluated on the parasite *Leishmania infantum*, the main causal agent of human visceral leishmaniasis in the Mediterranean basin and Latin America.

Cultures of promastigotes and axenic amastigotes of *Leishmania infantum* (MHOM/MA/67/ITMAP-236) expressing the luciferase gene were used. Evaluation of the metabolic activity of the parasites is based on oxidation of luciferin by luciferase in the presence of ATP. This process leads to the emission of photons which is proportional to the concentration of unlysed parasites.

Figure 2:
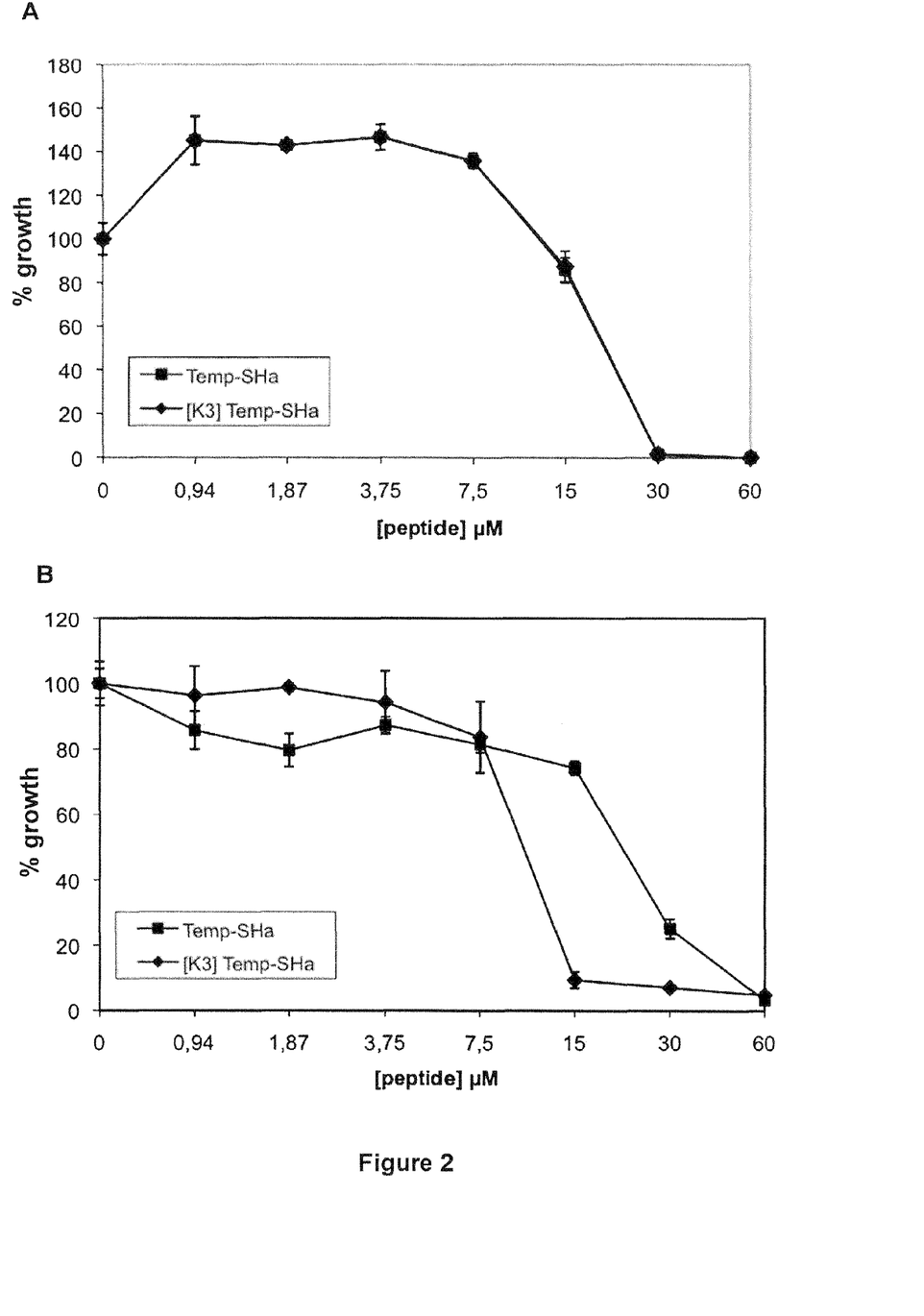
FIG. 2 is a graph depicting the activity of temporin-SHa (■) and the analog [K$^3$]temporin-SHa (♦) on axenic amastigotes (A) and promastigotes (B) of *Leishmania infantum*. The percentage growth of the amastigotes and promastigotes is plotted as a function of peptide concentration.

The results of these anti-*Leishmania* tests show that temporin-SHa and the analog [K³]temporin-SHa are active against the two forms of the parasite *Leishmania infantum* (FIGS. 2 A and B). However, the analog [K³]temporin-SHa has superior antiparasitic activity against promastigotes as compared to temporin-SHa. The analog [K³]temporin-SHa acts on the promastigote form of the parasite with an $IC_{50}$ of roughly 10 µM, whereas temporin-SHa has an $IC_{50}$ of approximately 20 µM (FIG. 2 B).

Figure 3:
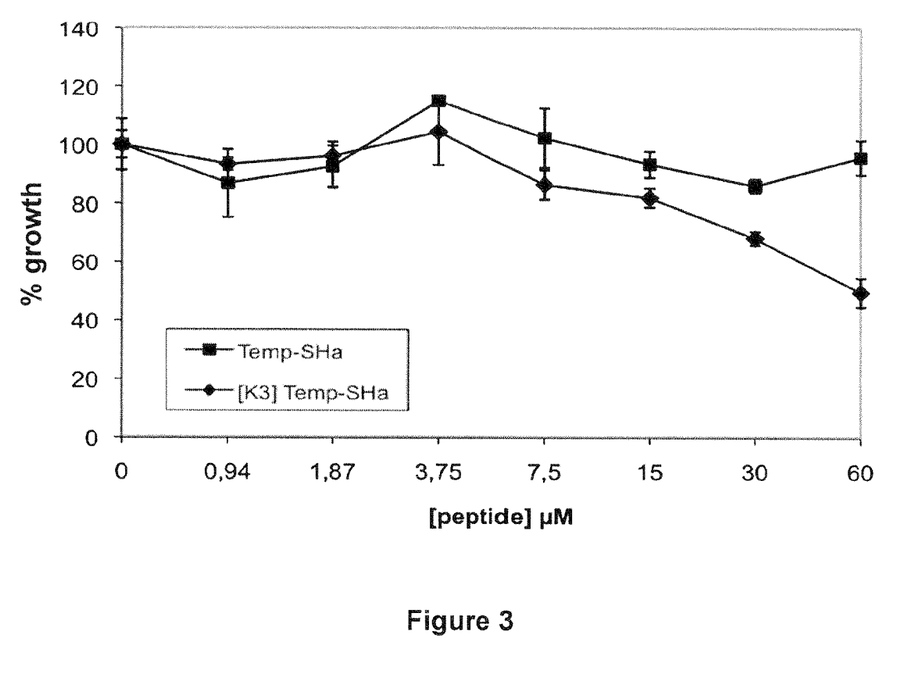
FIG. 3 is a graph illustrating the cytotoxic activity of temporin-SHa (■) and the analog [K$^3$]temporin-SHa (♦) on monocytes. The percentage of monocyte growth is plotted as a function of peptide concentration.

The cytotoxic effects of temporin-SHa and the analog [K³]temporin-SHa were evaluated on human THP-1 monocyte cell line. Monocytes are an undifferentiated form of macrophages which are the host cells of *Leishmania* parasites. The results (FIG. 3) show that temporin-SHa and the analog [K³]temporin-SHa are not cytotoxic at antimicrobial concentrations.

CONCLUSION

Substitution of the serine on the polar face of the α helix of temporin-SHa by lysine generated the analog [K³]temporin-SHa displaying more potent antimicrobial activity than temporin-SHa, particularly against Gram-negative bacteria and yeasts. This analog also has better antiparasitic activity against the parasite *Leishmania infantum*, in particular against promastigotes.

Moreover, it was shown that this increased antimicrobial potency is accompanied by a twofold reduction in hemolytic activity and that this analog is not cytotoxic to monocytes, the target cells of the parasite in the vertebral host, at antimicrobial concentrations.

BIBLIOGRAPHIC REFERENCES

Abbassi F, Oury B, Blasco T, Sereno D, Bolbach G, Nicolas P, Hani K, Amiche M, Ladram A (2008) Isolation, characterization and molecular cloning of new temporins from the skin of the North African ranid *Pelophylax saharica*. Peptides 29: 1526-33.

Brun R, Schönenberger M (1979) Cultivation and in vitro cloning or procyclic culture forms of *Trypanosoma brucei* in a semi-defined medium. Acta Trop. 36: 289-92.

Bevan M (1984) Binary *Agrobacterium* vectors for plant transformation. Nucleic Acids Res. 12: 8711-21.

Chinchar V G, Bryan L, Silphadaung U, Noga E, Wade D, Rollins-Smith L (2004) Inactivation of viruses infecting ectothermic animals by amphibian and piscine antimicrobial peptides, Virology 323: 268-75, Cirioni O, Giacometti A, Ghiselli R, Dell'Acqua G, Gov Y, Kamysz W, Lukasiak J, Mocchegiani F, Orlando F, D'Amato G, Balaban N, Saba V, Scalise G (2003) Prophylactic efficacy of topical temporin A and RNAIII inhibiting peptide in a subcutaneous rat Pouch model of graft infection attributable to *Staphylococci* with intermediate resistance to glycopeptides. Circulation 108: 767-71.

Conlon J M (2008) Reflections on a systematic nomenclature for antimicrobial peptides from the skins of frogs of the family Ranidae. Peptides 29: 1815-9.

Conlon J M, Kolodziejek J, Nowotny N (2009) Antimicrobial peptides from the skins of North American frogs. Biochim. Biophys. Acta, 1788: 1556-63.

Dennison S R, Wallace J, Harris F, Phoenix D A (2005) Amphiphilic α-helical antimicrobial peptides and their structure/function relationships. Protein Pept. Lett. 12: 31-9.

Giangaspero A, Sandri L, Tossi A (2001) Amphipathic α helical antimicrobial peptides: A systematic study of the effects of structural and physical properties on biological activity. Eur. J. Biochem. 268: 5589-600.

Hajdukiewicz P, Svab Z, Maliga P (1994) The small, versatile pPZP family of *Agrobacterium* binary vectors for plant transformation. Plant Mol. Biol. 25: 989-94.

Hooykaas P J J, Schilperoort R A (1992) *Agrobacterium* and plant genetic engineering. Plant Mol. Biol. 19: 15-38.

Isaacson T, Soto A, Iwamuro S, Knoop F C, Conlon J M (2002) Antimicrobial peptides with atypical structural features from the skin of the Japanese brown frog *Rana japonica*. Peptides 23: 419-25.

Kim J B, Iwamuro S, Knoop F C, Conlon J M (2001) Antimicrobial peptides from the skin of the Japanese mountain brown frog, *Rana ornativentris*. J. Pept. Res. 58: 349-56.

Kullmann W (1987) Enzymatic peptide synthesis, CRC Press, Florida.

Mangoni M L (2006) Temporins, anti-infective peptides with expanding properties. Cell. Mol. Life. Sci. 63: 1060-9.

Mosmann T (1983) Rapid colorimetric assay for cellular growth and survival: application to proliferation and cytotoxicity assays. J. Immunol. Methods 65: 55-63.

Rollins-Smith L A, Carey C, Conlon J M, Reinert L K, Doersam J K, Bergman T et al (2003) Activities of temporin family peptides against the chytrid fungus (*Batrachochytrium dendrobatidis*) associated with global amphibian declines. Antimicrob. Agents Chemother. 47: 1157-60.

Roy G, Dumas C, Sereno D, Wu Y, Singh. A K, Tremblay M J, Ouellette M, Olivier M, Papadopoulou B (2000) Episomal and stable expression of the luciferase reporter gene for quantifying *Leishmania* spp. infections in macrophages and in animal models. Mol. Biochem. Parasitol. 110: 195-206.

Russell J A, Roy M K, Sanford J C (1992) Major improvements in biolistic transformation of suspension-cultured tobacco cells. In Vitro Cell. Dev. Biol., 28P, p. 97-105.

Sambrook J, Russell D (2001) Molecular cloning: a laboratory manual, Third Edition Cold Spring Harbor.

Sereno D, Lemesre J L (1997) Axenically cultured amastigote forms as an in vitro model for investigation of antileishmanial agents. Antimicrob. Agents Chemother. 41: 972-6.

Siemens, J, Schieder O (1996) Transgenic plants: genetic transformation—recent developments and the state of the art. Plant Tissue Cult. Biotechnol. 2: 66-75.

Simmaco M, De Biase G, Severini C, Aita M, Falconieri G, Erspamer, Barra D, Bossa F (1990) Purification and characterization of bioactive peptides from skin extract of *Rana esculenta*. Biochem. Biophys. Acta 1033: 318-23.

Simmaco M, Mignogna G, Canofeni S, Miele R, Mangoni M L, Barra D (1996) Temporins, antimicrobial peptides from the European red frog *Rana temporaria*. Eur. J. Biochem. 242: 788-92.

Vanhoye D, Bruston F, El Amri S, Ladram A, Amiche M, Nicolas P (2004) Membrane association, electrostatic sequestration and cytotoxicity of Gly-Leu-rich peptide orthologs with differing functions. Biochemistry 43: 8391-409.

Yeaman M R, Yount N Y (2003) Mechanisms of antimicrobial peptide action and resistance. Pharmacol. Rev. 55: 27-55,

---

The invention claimed is:

1. A non-natural peptide of between 13 and 100 amino acids selected from the group consisting of:
   a) a peptide containing the sequence F-L-$X_1$-G-I-V-G-M-L-G-K-L-F (SEQ ID NO: 2) or a pharmaceutically acceptable salt thereof;
   b) a retropeptide or retro-inverso peptide of a peptide containing the sequence F-L-$X_1$-G-I-V-G-M-L-G-K-L-F (SEQ ID NO: 2) or a pharmaceutically acceptable salt thereof; and
   c) a peptide containing the sequence of SEQ ID NO: 2 shortened by 1 or 2 amino acids at the N-terminal end or a pharmaceutically acceptable salt thereof;
   wherein said non-natural peptide or said pharmaceutically acceptable salt thereof as shown in group a), b) and c) exhibits antimicrobial activity and wherein $X_1$ is an amino acid selected from the group consisting of R (arginine), H (histidine) and K (lysine).

2. The non-natural peptide according to claim 1, wherein $X_1$ represents K (lysine).

3. A method for treating a microbial infection comprising administering a therapeutically effective dose of a non-natural peptide according to claim 1 to a subject in need of treatment for said microbial infection.

4. The method according to claim 3, wherein the microbial infection is an infection due to a bacterium, a virus, a fungus or a parasite.

5. The method according to claim 4, wherein the parasite belongs to the genus *Leishmania*.

6. A method for treating an infection of a plant by a phytopathogen comprising administering an effective dose of a non-natural peptide according to claim 1 to said plant.

7. A method for improving conservation of a food product comprising applying an effective dose of a non-natural peptide according to claim 1 to said food product.

8. A method of disinfecting a surface, a liquid or a gas comprising applying an effective dose of a non-natural peptide according to claim 1 to said surface, liquid or gas.

9. The non-natural peptide according to claim 1, wherein $X_1$ represents H (histidine).

10. The non-natural peptide according to claim 1, wherein $X_1$ represents R (arginine).

11. The non-natural peptide according to claim 1, wherein said non-natural peptide has a size of 13 amino acids.

12. The non-natural peptide according to claim 1, wherein said non-natural peptide contains the amino acid sequence of SEQ ID NO: 2.

13. The non-natural peptide according to claim 1, wherein said non-natural peptide is a retropeptide or retro-inverso peptide of a peptide containing the amino acid sequence of SEQ ID NO: 2.

14. The non-natural peptide according to claim 1, wherein said non-natural peptide contains the amino acid sequence of SEQ ID NO: 2 shortened by 1 or 2 amino acids at the N-terminal end.

15. The non-natural peptide according to claim 1, wherein said pharmaceutically acceptable salt is a hydrochloric acid salt, hydrobromic acid salt, sulphuric acid salt, phosphoric acid salt; acetic acid salt, citric acid salt, maleic acid salt, malic acid salt, succinic acid salt, ascorbic acid salt, tartaric acid salt, sodium salt, potassium salt, calcium salt, magnesium salt or ammonium salt.

* * * * *

UNITED STATES PATENT AND TRADEMARK OFFICE
CERTIFICATE OF CORRECTION

| | | |
|---|---|---|
| PATENT NO. | : 9,522,942 B2 | Page 1 of 1 |
| APPLICATION NO. | : 13/257018 | |
| DATED | : December 20, 2016 | |
| INVENTOR(S) | : Ali Ladram et al. | |

It is certified that error appears in the above-identified patent and that said Letters Patent is hereby corrected as shown below:

In the Specification

Column 4,
Line 14, "the a helix" should read --the α helix--.

Column 15,
Line 16, "7 day's" should read --7 days--.

Column 20,
Line 19, "27-55," should read --27-55.--.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 19

<210> SEQ ID NO 1
<211> LENGTH: 13
<212> TYPE: PRT
<213> ORGANISM: Pelophylax saharica

<400> SEQUENCE: 1

Phe Leu Ser Gly Ile Val Gly Met Leu Gly Lys Leu Phe
1               5                   10

<210> SEQ ID NO 2
<211> LENGTH: 13
<212> TYPE: PRT
<213> ORGANISM: Artificial
<220> FEATURE:
<223> OTHER INFORMATION: Peptide analogue of temporin-SHa
<220> FEATURE:
<221> NAME/KEY: MISC_FEATURE
<222> LOCATION: (3)..(3)
<223> OTHER INFORMATION: R, H ou K

<400> SEQUENCE: 2

Phe Leu Xaa Gly Ile Val Gly Met Leu Gly Lys Leu Phe
1               5                   10

<210> SEQ ID NO 3
<211> LENGTH: 13
<212> TYPE: PRT
<213> ORGANISM: Artificial
<220> FEATURE:
<223> OTHER INFORMATION: Peptide analogue of temporin-SHa
<220> FEATURE:
<221> NAME/KEY: MISC_FEATURE
<222> LOCATION: (4)..(4)
<223> OTHER INFORMATION: R, H ou K

<400> SEQUENCE: 3

Phe Leu Ser Xaa Ile Val Gly Met Leu Gly Lys Leu Phe
1               5                   10

<210> SEQ ID NO 4
<211> LENGTH: 13
<212> TYPE: PRT
<213> ORGANISM: Artificial
<220> FEATURE:
<223> OTHER INFORMATION: Peptide analogue of temporin-SHa
```

```
<220> FEATURE:
<221> NAME/KEY: MISC_FEATURE
<222> LOCATION: (7)..(7)
<223> OTHER INFORMATION: R, H ou K

<400> SEQUENCE: 4

Phe Leu Ser Gly Ile Val Xaa Met Leu Gly Lys Leu Phe
1               5                   10

<210> SEQ ID NO 5
<211> LENGTH: 13
<212> TYPE: PRT
<213> ORGANISM: Artificial
<220> FEATURE:
<223> OTHER INFORMATION: Peptide analogue of temporin-SHa
<220> FEATURE:
<221> NAME/KEY: MISC_FEATURE
<222> LOCATION: (10)..(10)
<223> OTHER INFORMATION: R, H ou K

<400> SEQUENCE: 5

Phe Leu Ser Gly Ile Val Gly Met Leu Xaa Lys Leu Phe
1               5                   10

<210> SEQ ID NO 6
<211> LENGTH: 13
<212> TYPE: PRT
<213> ORGANISM: Artificial
<220> FEATURE:
<223> OTHER INFORMATION: Peptide analogue of temporin-SHa
<220> FEATURE:
<221> NAME/KEY: MISC_FEATURE
<222> LOCATION: (3)..(4)
<223> OTHER INFORMATION: R, H ou K

<400> SEQUENCE: 6

Phe Leu Xaa Xaa Ile Val Gly Met Leu Gly Lys Leu Phe
1               5                   10

<210> SEQ ID NO 7
<211> LENGTH: 13
<212> TYPE: PRT
<213> ORGANISM: Artificial
<220> FEATURE:
<223> OTHER INFORMATION: Peptide analogue of temporin-SHa
<220> FEATURE:
<221> NAME/KEY: MISC_FEATURE
<222> LOCATION: (3)..(3)
<223> OTHER INFORMATION: R, H ou K
<220> FEATURE:
<221> NAME/KEY: MISC_FEATURE
<222> LOCATION: (7)..(7)
<223> OTHER INFORMATION: R, H ou K

<400> SEQUENCE: 7

Phe Leu Xaa Gly Ile Val Xaa Met Leu Gly Lys Leu Phe
1               5                   10

<210> SEQ ID NO 8
<211> LENGTH: 13
<212> TYPE: PRT
<213> ORGANISM: Artificial
<220> FEATURE:
<223> OTHER INFORMATION: Peptide analogue of temporin-SHa
<220> FEATURE:
<221> NAME/KEY: MISC_FEATURE
<222> LOCATION: (3)..(3)
<223> OTHER INFORMATION: R, H ou K
<220> FEATURE:
<221> NAME/KEY: MISC_FEATURE
<222> LOCATION: (10)..(10)
```

<223> OTHER INFORMATION: R, H ou K

<400> SEQUENCE: 8

Phe Leu Xaa Gly Ile Val Gly Met Leu Xaa Lys Leu Phe
1               5                   10

<210> SEQ ID NO 9
<211> LENGTH: 13
<212> TYPE: PRT
<213> ORGANISM: Artificial
<220> FEATURE:
<223> OTHER INFORMATION: Peptide analogue of temporin-SHa
<220> FEATURE:
<221> NAME/KEY: MISC_FEATURE
<222> LOCATION: (4)..(4)
<223> OTHER INFORMATION: R, H ou K
<220> FEATURE:
<221> NAME/KEY: MISC_FEATURE
<222> LOCATION: (7)..(7)
<223> OTHER INFORMATION: R, H ou K

<400> SEQUENCE: 9

Phe Leu Ser Xaa Ile Val Xaa Met Leu Gly Lys Leu Phe
1               5                   10

<210> SEQ ID NO 10
<211> LENGTH: 13
<212> TYPE: PRT
<213> ORGANISM: Artificial
<220> FEATURE:
<223> OTHER INFORMATION: Peptide analogue of temporin-SHa
<220> FEATURE:
<221> NAME/KEY: MISC_FEATURE
<222> LOCATION: (4)..(4)
<223> OTHER INFORMATION: R, H ou K
<220> FEATURE:
<221> NAME/KEY: MISC_FEATURE
<222> LOCATION: (10)..(10)
<223> OTHER INFORMATION: R, H ou K

<400> SEQUENCE: 10

Phe Leu Ser Xaa Ile Val Gly Met Leu Xaa Lys Leu Phe
1               5                   10

<210> SEQ ID NO 11
<211> LENGTH: 13
<212> TYPE: PRT
<213> ORGANISM: Artificial
<220> FEATURE:
<223> OTHER INFORMATION: Peptide analogue of temporin-SHa
<220> FEATURE:
<221> NAME/KEY: MISC_FEATURE
<222> LOCATION: (7)..(7)
<223> OTHER INFORMATION: R, H ou K
<220> FEATURE:
<221> NAME/KEY: MISC_FEATURE
<222> LOCATION: (10)..(10)
<223> OTHER INFORMATION: R, H ou K

<400> SEQUENCE: 11

Phe Leu Ser Gly Ile Val Xaa Met Leu Xaa Lys Leu Phe
1               5                   10

<210> SEQ ID NO 12
<211> LENGTH: 13
<212> TYPE: PRT
<213> ORGANISM: Artificial
<220> FEATURE:
<223> OTHER INFORMATION: Peptide analogue of temporin-SHa
<220> FEATURE:
<221> NAME/KEY: MISC_FEATURE

```
<222> LOCATION: (3)..(4)
<223> OTHER INFORMATION: R, H ou K
<220> FEATURE:
<221> NAME/KEY: MISC_FEATURE
<222> LOCATION: (7)..(7)
<223> OTHER INFORMATION: R, H ou K

<400> SEQUENCE: 12

Phe Leu Xaa Xaa Ile Val Xaa Met Leu Gly Lys Leu Phe
1               5                   10

<210> SEQ ID NO 13
<211> LENGTH: 13
<212> TYPE: PRT
<213> ORGANISM: Artificial
<220> FEATURE:
<223> OTHER INFORMATION: Peptide analogue of temporin-SHa
<220> FEATURE:
<221> NAME/KEY: MISC_FEATURE
<222> LOCATION: (3)..(4)
<223> OTHER INFORMATION: R, H ou K
<220> FEATURE:
<221> NAME/KEY: MISC_FEATURE
<222> LOCATION: (10)..(10)
<223> OTHER INFORMATION: R, H ou K

<400> SEQUENCE: 13

Phe Leu Xaa Xaa Ile Val Gly Met Leu Xaa Lys Leu Phe
1               5                   10

<210> SEQ ID NO 14
<211> LENGTH: 13
<212> TYPE: PRT
<213> ORGANISM: Artificial
<220> FEATURE:
<223> OTHER INFORMATION: Peptide analogue of temporin-SHa
<220> FEATURE:
<221> NAME/KEY: MISC_FEATURE
<222> LOCATION: (3)..(3)
<223> OTHER INFORMATION: R, H ou K
<220> FEATURE:
<221> NAME/KEY: MISC_FEATURE
<222> LOCATION: (7)..(7)
<223> OTHER INFORMATION: R, H ou K
<220> FEATURE:
<221> NAME/KEY: MISC_FEATURE
<222> LOCATION: (10)..(10)
<223> OTHER INFORMATION: R, H ou K

<400> SEQUENCE: 14

Phe Leu Xaa Gly Ile Val Xaa Met Leu Xaa Lys Leu Phe
1               5                   10

<210> SEQ ID NO 15
<211> LENGTH: 13
<212> TYPE: PRT
<213> ORGANISM: Artificial
<220> FEATURE:
<223> OTHER INFORMATION: Peptide analogue of temporin-SHa
<220> FEATURE:
<221> NAME/KEY: MISC_FEATURE
<222> LOCATION: (4)..(4)
<223> OTHER INFORMATION: R, H ou K
<220> FEATURE:
<221> NAME/KEY: MISC_FEATURE
<222> LOCATION: (7)..(7)
<223> OTHER INFORMATION: R, H ou K
<220> FEATURE:
<221> NAME/KEY: MISC_FEATURE
<222> LOCATION: (10)..(10)
<223> OTHER INFORMATION: R, H ou K

<400> SEQUENCE: 15
```

```
Phe Leu Ser Xaa Ile Val Xaa Met Leu Xaa Lys Leu Phe
1               5                   10
```

<210> SEQ ID NO 16
<211> LENGTH: 13
<212> TYPE: PRT
<213> ORGANISM: Artificial
<220> FEATURE:
<223> OTHER INFORMATION: Peptide analogue of temporin-SHa
<220> FEATURE:
<221> NAME/KEY: MISC_FEATURE
<222> LOCATION: (3)..(4)
<223> OTHER INFORMATION: R, H ou K
<220> FEATURE:
<221> NAME/KEY: MISC_FEATURE
<222> LOCATION: (7)..(7)
<223> OTHER INFORMATION: R, H ou K
<220> FEATURE:
<221> NAME/KEY: MISC_FEATURE
<222> LOCATION: (10)..(10)
<223> OTHER INFORMATION: R, H ou K

<400> SEQUENCE: 16

```
Phe Leu Xaa Xaa Ile Val Xaa Met Leu Xaa Lys Leu Phe
1               5                   10
```

<210> SEQ ID NO 17
<211> LENGTH: 50
<212> TYPE: PRT
<213> ORGANISM: Artificial
<220> FEATURE:
<223> OTHER INFORMATION: Precursor of a mature antimicrobial peptide
<220> FEATURE:
<221> NAME/KEY: MISC_FEATURE
<222> LOCATION: (38)..(38)
<223> OTHER INFORMATION: S, R, H ou K
<220> FEATURE:
<221> NAME/KEY: MISC_FEATURE
<222> LOCATION: (39)..(39)
<223> OTHER INFORMATION: G, R, H ou K
<220> FEATURE:
<221> NAME/KEY: MISC_FEATURE
<222> LOCATION: (42)..(42)
<223> OTHER INFORMATION: G, R, H ou K
<220> FEATURE:
<221> NAME/KEY: MISC_FEATURE
<222> LOCATION: (45)..(45)
<223> OTHER INFORMATION: G, R, H ou K

<400> SEQUENCE: 17

```
Phe Leu Gly Thr Ile Asn Leu Ser Leu Cys Glu Gln Glu Arg Asp Ala
1               5                   10                  15

Asp Glu Glu Glu Arg Arg Asp Glu Pro Asn Glu Ser Asn Val Glu Val
            20                  25                  30

Glu Lys Arg Phe Leu Xaa Xaa Ile Val Xaa Met Leu Xaa Lys Leu Phe
        35                  40                  45

Gly Lys
    50
```

<210> SEQ ID NO 18
<211> LENGTH: 13
<212> TYPE: PRT
<213> ORGANISM: Artificial
<220> FEATURE:
<223> OTHER INFORMATION: Peptide analogue of temporin-SHa
<220> FEATURE:
<221> NAME/KEY: MISC_FEATURE
<222> LOCATION: (3)..(3)
<223> OTHER INFORMATION: S, R, H ou K
<220> FEATURE:

```
<221> NAME/KEY: MISC_FEATURE
<222> LOCATION: (4)..(4)
<223> OTHER INFORMATION: G, R, H ou K
<220> FEATURE:
<221> NAME/KEY: MISC_FEATURE
<222> LOCATION: (7)..(7)
<223> OTHER INFORMATION: G, R, H ou K
<220> FEATURE:
<221> NAME/KEY: MISC_FEATURE
<222> LOCATION: (10)..(10)
<223> OTHER INFORMATION: G, R, H ou K

<400> SEQUENCE: 18

Phe Leu Xaa Xaa Ile Val Xaa Met Leu Xaa Lys Leu Phe
1               5                   10

<210> SEQ ID NO 19
<211> LENGTH: 13
<212> TYPE: PRT
<213> ORGANISM: Artificial
<220> FEATURE:
<223> OTHER INFORMATION: Analogue [K3]temporin-Sha

<400> SEQUENCE: 19

Phe Leu Lys Gly Ile Val Gly Met Leu Gly Lys Leu Phe
1               5                   10
```